United States Patent [19]

Hubbard et al.

[11] Patent Number: 5,066,595
[45] Date of Patent: Nov. 19, 1991

[54] PROCESS FOR INCREASING FREE POOL LYSINE CONTENT IN MAIZE

[75] Inventors: Ernest T. Hubbard, Sunnyvale; Michele D. Hollingsworth, Santa Cruz; N. V. Raghava Ram, Cupertino, all of Calif.; Judith P. Cook, Madison, Wis.

[73] Assignee: Sungene Technologies Corporation, Palo Alto, Calif.

[21] Appl. No.: 433,414

[22] Filed: Nov. 7, 1989

Related U.S. Application Data

[63] Continuation of Ser. No. 939,005, Dec. 8, 1986, abandoned.

[51] Int. Cl.$^5$ ................................. C12N 5/00
[52] U.S. Cl. ..................... 435/240.45; 435/240.49; 435/240.5; 435/240.54; 435/240.48
[58] Field of Search ................. 435/240.48, 240.49, 435/240.45, 240.5, 240.54

[56] References Cited

U.S. PATENT DOCUMENTS

4,642,411  2/1987  Hibberd et al. .................... 800/200

FOREIGN PATENT DOCUMENTS

177738  4/1986  European Pat. Off. .

OTHER PUBLICATIONS

Green et al. 1980, Crop Sci. 20:358.
Green et al. 1975, Crop Sci. 15:417.
Schaffer et al. 1981. In Vitro 17:345.
Mertz et al., *Science* 145, 279 (1964).
Nelson et al., *Science* 150, 1469 (1965).
Nelson, *Genet. Agrar.* 21, 209, (1967).
Green et al., *Crop Science* 15, 417 (1975).
Green et al., *Crop Science* 20, 358 (1980).
Singh et al., *Crop Science* 15, 79 (1975).
Hibberd et al., *Planta.* 148, 183 (1980).
Hibberd, Thesis (1979).
Hibberd et al., *Proc. Nat. Acad. Sci. USA* 78, 559 (1982).
Phillips et al., *Crop Science* 21, 601 (1981).
Green et al., *Crop Science* 14, 827 (1974).
Freeling et al., *Maydica* 21, 97 (1976).
Vasil et al., *Theor. Appl. Genet.* 66, 285 (1983).
Edallo et al., *Maydica* 26, 39 (1981).
Lu et al., *Theor. Appl. Genet.* 62, 109 (1982).
Gengenbach et al., *Proc. Nat. Acad. Sci. USA* 74, 5113 (1977).
Green et al., *Crop Science* 14, 54 (1974).
Duncan et al., *Planta* 165, 322 (1985).
Widholm, *Can. J. Bot.* 54, 1523 (1976).
Das et al., *Plant Cell Culture in Crop Improvement*, 411–418, Edited by S. K. Sen & K. L. Giles, New York, NY (1982).
Matthews et al., *Z. Pflanzenphysiol. Bd.* 96, 453 (1980).
Negrutiu et al., *Theor. Appl. Genet.* 68, 11 (1984).
Widholm, *J. Exper. Bot.* 29, 111 (9178).
Gonzales et al., *Plant Physiol.* 74, 640 (1984).
Ranch et al., *Plant Physiol.* 71, 136 (1983).
Widholm, *Biochim. Biophys. Acta.* 278, 48 (1972).
Carlson et al., *Physiol. Plant.* 44, 251 (1978).
Widholm, *Biochim. Biophys. Acta.* 261, 52 (1972).
Widholm, *Biochim. Biophys. Acta.* 25, 75 (1971).

*Primary Examiner*—Elizabeth C. Weimar
*Assistant Examiner*—David T. Fox
*Attorney, Agent, or Firm*—Venable, Baetjer, Howard & Civiletti

[57] ABSTRACT

The present invention is directed to a process for increasing the free pool lysine content of individual maize seeds and for increasing the average free pool lysine content of seeds produced by a maize plant. The process, in general, comprises initiating callus from maize tissue, selecting for callus tissue resistant to S-2-aminoethyl-L-cysteine, and regenerating plants from the selected callus. In addition, the callus may be maintained before or during the selection scheme, or in place of the selection scheme.

54 Claims, No Drawings

PROCESS FOR INCREASING FREE POOL LYSINE CONTENT IN MAIZE

This application is a continuation of application Ser. No. 939,005, filed Dec. 8, 1986, now abandoned.

BACKGROUND OF THE INVENTION

1. Field of the Invention

The present invention relates to a process for increasing the free pool lysine content in maize through selection in tissue culture.

2. Description of the Prior Art

Cereal grains are a major source of vegetable protein. Maize (*Zea mays* L.) contributes approximately one-fourth of the total cereal protein produced. However, maize has a low content of certain essential amino acids, especially lysine, methionine and typtophan. As a result, maize in the diet must be supplemented with food containing these amino acids in order to provide a balanced diet. One goal of plant breeding in maize has been to increase the amount of lysine and tryptophan present in the seed. At least two approaches can be visualized to accomplish an increase in these amino acids. The first approach is to increase the lysine or tryptophan content in the proteins found in the maize kernel. The second is to increase the free pool (endogenous) lysine or tryptophan content within the maize kernel.

The first significant breeding results with regard to changes of the protein composition of maize kernels in the direction desired was the discovery by Mertz, E. J., et al. (*Science* 145, 279 (1964)) that the protein composition of maize endosperm could be drastically changed by a single gene (opaque-2). In the following year, the same authors reported a second mutant gene (floury-2) which changed the protein composition of maize endosperm in a similar way (Nelson, O. E., et al., *Science* 150, 1469 (1965)). It was found that, besides similar changes in lysine and tryptophan, floury-2 also has a higher methionine content.

It has been demonstrated (Nelson, O. E., *Genet.Agron.* 21, 209 (1967)) that the different amino acid composition of the two maize mutants is chiefly due to the modification of the relative amounts of protein fractions, i.e., a partial suppression of the prolamine and its replacement by other fractions rich in lysine and tryptophan.

Considering the agronomic performance and especially the yield, it seems that opaque-2 is somewhat inferior to normal maize, chiefly due to its lighter kernels. In populations where opaque-2 had been introduced into inbred lines, it has been found that the percentage weight loss of opaque-2 kernels as compared to normal sibs varied from less than 5% to 40%, depending on the inbred line.

Although opaque-2 stocks produce in general smaller and lighter kernels than normal stocks, it has been pointed out that it would be unsafe to conclude that opaque-2 types have necessarily a lower yield than normal isogenic types. The data indicate that modifier genes affect kernel size in opaque-2 homozygotes; therefore appropriate selection in segregating populations should be effective in improving that trait. Other researchers are of a similar opinion and point out that the density of opaque-2 kernels is dependent on the genetic background which would make it possible to select lines in which opaque-2 shows higher densities.

The opaque-2 gene has been incorporated into corn hybrids which commonly had a lower yield than their normal hybrid counterparts. Recently, however, improvements in yield have spurred renewed interest in high lysine corn usage.

Although much effort has been expended to increase the lysine content of maize proteins, very little effort has gone towards the increase of lysine content in maize by increasing the free pool lysine content.

Plant regeneration from cells in culture is essential for the application of somatic hybridization, for the production of new varieties through somoclonal variation or in vitro selection, and for the use of genetic engineering in producing new varieties. Although plants can be regenerated from tissue culture of several varieties of corn, there are many varieties for which this has not been accomplished using similar techniques.

In recent years, plant cell culture successes have had a considerable influence on the understanding of the respective roles of cell and organism in control of plant growth and development. Isolated plant cells have been shown to be amenable to in vitro culture and complete plants have been regenerated from cultures derived from somatic tissues, either directly via somatic embryogenesis or indirectly via organogenesis. Generally, the regeneration pathway of choice is determined empirically by the manipulation of extrinsic factors, especially growth regulators. Early investigations of certain plant species have suggested that exogenous auxin concentration is a major factor controlling somatic embryogenesis, such that its reduction leads to the initiation of embryoid formation. In other species, exposure to a definite balance of auxin and cytokinin leads to the occurrence of organogenesis (shoots, then roots). Although several genotypes of corn have been regenerated using these techniques, no process is generally applicable to most genotypes of corn. Many genotypes remain extremely difficult, if not impossible, to culture using the prior processes.

The process which has become the standard system for corn tissue culture is described by Green et al., *Crop Science* 15, 417 (1975). In this process, immature embryos were plated onto a callus induction medium which comprises the MS mineral salts, Straus vitamins and amino acids (glycine, asparagine, niacin, thiamine, pyridoxine and pantothenic acid), 2% sucrose, 0.8% agar and a hormone selected from 2,4-dichlorophenoxyacetic acid (2,4-D), p-chlorophenoxyacetic acid (p-CPA), α-naphthaleneacetic acid (NAA), 2-isopentyladenine (2-ip) or mixtures thereof. Hormone concentrations which were useful were 2 mg/l 2,4-D and a mixture of 1 mg/l 2,4-D, 4 mg/l NAA and 0.05 mg/l 2-ip. Plantlets were regenerated by subculturing the callus on medium containing reduced hormone concentrations. Regeneration was then accomplished on medium containing 0.25 mg/l 2,4-D or a mixture of 1 mg/l NAA and 0.05 mg/l 2-ip, respectively. All culturing was conducted in a 16 hour light/8 hour dark cycle for 3-4 week intervals before transfer. This reference reports that callus induction did not occur in one of five genotypes tested.

Similar results with different media have been demonstrated by Freeling et al., *Maydica* 21, 97 (1976); Vasil et al., *Theor.Appl. Genet.* 66, 285 (1983); Edallo et al., *Maydica* 26, 39 (1981); Lu et al., *Theor.Appl.Genet.* 62, 109 (1982); Gegenbach et al., *Proc.Nat. Acad.Sci.USA* 74, 5113 (1977); and Green et al., *Crop Science* 14, 54

(1974). The latter reference also demonstrates genotype effects on callus induction.

Although this procedure has generally been unsuccessful for regenerating plants from all maize genotypes, the regeneration of most genotypes is now possible through the substitution of dicamba for 2,4-D in the media. See published European Application No. 0 177 738 and Duncan et al., *Planta* 165, 322 (1985).

SUMMARY OF THE INVENTION

The present invention is directed to a process for increasing the free pool lysine content in maize seed and for increasing the average free pool lysine content of seeds produced by a maize plant. The process comprises the regeneration of plants from tissue in culture which has been selected through the use of a lysine analog. More specifically, the present process comprises the steps of:

(a) culturing tissue obtained from a maize plant on a callus induction medium comprising mineral salts, vitamins, sucrose and a hormone to form callus;

(b) subculturing said callus on selection medium comprising mineral salts, vitamins, sucrose, S-2-aminoethyl-L-cysteine (AEC) and a hormone to produce selected callus; and (c) subculturing said selected callus on regeneration medium comprising mineral salts, vitamins and sucrose to regenerate plants.

Alternatively, the process can comprise the additional step of subculturing the callus maintenance medium comprising mineral salts, vitamins, sucrose and a hormone before subculturing on the selection medium.

The plants are grown to produce seed ($R_1$) which can be used to produce further generations of plants.

DETAILED DESCRIPTION OF THE INVENTION

The present invention is directed to a process for increasing the free pool lysine content in maize seed and for increasing the average free pool lysine content of seeds produced by a maize plant. The process utilizes tissue culture selection of maize tissue with AEC as described further below.

The present invention is directed to maize seeds which have a free pool lysine content of at least about 500 $\mu$g per gram dry seed weight. Preferably, each seed has at least about 600 $\mu$g of free pool lysine per gram dry seed weight. In the most preferred embodiment, each seed has at least 700 $\mu$g of free pool lysine per gram dry seed weight.

The present invention is further directed to maize plants, each of which produces seeds having an average free pool lysine content of at least about 325 $\mu$g per gram dry seed weight. Preferably, each plant produces seeds having an average free pool lysine content of at least about 400 $\mu$g per gram dry seed weight. It is most preferred that the average free pool lysine content be at least about 500 $\mu$g per gram dry seed weight. It should be evident that "average free pool lysine content" refers to the average of the free pool lysine content of the individual seeds produced by the maize plant.

The initial regenerated plants ($R_0$) are produced from tissue culture generally by regenerating plants from tissue in culture which has been selected through the use of a lysine analog, S-2-aminoethyl-L-cysteine (AEC). It is also possible to isolate plants which meet the desired characteristics without the use of an AEC selection scheme. The following generations of plants can be produced by germinating the seed ($R_1$ seed) produced by the $R_0$ plants. The $R_1$ plants can be self-pollinated to produce $R_2$ seeds. Alternatively, the $R_1$ plants can be incorporated into a breeding program to produce hybrids, inbreds, etc. Any generation of plants having the initial $R_1$ seed as a parent can be used to develop hybrids or inbreds, etc.

For example, if possible, the regenerated plants or their progeny are self-pollinated. In addition, pollen obtained from the regenerated plants or their progeny is crossed to seed grown plants of agronomically important inbred lines. In some cases, pollen from plants of these inbred lines is used to pollinate regenerated plants or their progeny. The trait is genetically characterized by evaluating the segregation of the trait in first-and later-generation progeny. The heritability and expression in plants of traits selected in tissue culture are of particular importance if the traits are to be commercially useful.

The commercial value of maize having an increased free pool lysine content is greatest if many different hybrid combinations are available for sale. The farmer typically grows more than one kind of hybrid based on such differences as maturity, standability or other agronomic traits. Additionally, hybrids adapted to one part of the corn belt are not adapted to another part because of differences in such traits as maturity, disease and insect resistance. Because of this, it is necessary to breed increased free pool lysine content into a large number of parental lines so that many hybrid combinations can be produced.

Adding the increased free pool lysine genotype to agronomically elite lines is most efficiently accomplished if the genetic control of free pool lysine content is understood. This requires crossing increased free pool lysine plants with low free pool lysine plants and studying the pattern of inheritance in segregating generations to ascertain whether the trait is expressed as a dominant or recessive, the number of genes involved, and any possible interaction between genes if more than one is required for expression. This genetic analysis can be part of the initial efforts to convert agronomically elite, yet low free pool lysine content, lines to increased free pool lysine lines.

A conversion process (backcrossing) is carried out by crossing the original increased free pool lysine line to normal elite lines and crossing the progeny back to the normal parent. The progeny from this cross will segregate such that some plants carry the gene(s) responsible for increased free pool lysine, whereas some do not. Plants carrying such genes will be crossed again to the normal parent, resulting in progeny which segregate for increased free pool lysine and normal production once more. This is repeated until the original normal parent has been converted to an increased free pool line, yet possesses all other important attributes as originally found in the normal parent. A separate backcrossing program is implemented for every elite line that is to be converted to an increased free pool lysine line.

Subsequent to the backcrossing, the new lines and the appropriate combinations of lines which make good commercial hybrids are evaluated for increased free pool lysine content as well as a battery of important agronomic traits. Increased free pool lysine lines and hybrids are produced which are true to type of the original normal lines and hybrids. This requires evaluation under a range of environmental conditions where the lines or hybrids will generally be grown commercially. For production of increased free pool lysine maize, it may be necessary that both parents of the hybrid seed corn be homozygous for the increased free pool lysine character. Parental lines of hybrids that perform satisfactorily are increased and used for hybrid production using standard hybrid seed corn production practices.

In general, the process to produce $R_0$ plants comprises (a) culturing maize tissue on a medium to produce callus; (b) selecting callus tissue which is resistant to AEC in the culture medium, and (c) regenerating plants from the selected callus. The callus can optionally be maintained on a maintenance medium prior to transfer to a selection medium. The regenerated plants are matured and self-pollinated to produce $R_1$ seeds. $R_2$ seeds are produced by self-pollinating $R_1$ plants germinated from $R_1$ seeds. Additional generations can be obtained in like manner.

Although the process to increase free pool lysine content generally uses a selection scheme with AEC, it is possible to produce maize seeds and plants having the desired characteristics without selection. In this instance, the callus is maintained on a maintenance medium rather than cultured on a selection medium. This process is not as efficient, i.e., it has a lower frequency of success than selection with AEC.

Within the general process outlined above, several tissue culture sequences can be utilized to produce maize seeds and plants having the desired characteristics. The preferred sequences can be summarized as follows:

In the first preferred sequence, callus is induced on a callus induction medium as described below. The callus is then transferred to maintenance medium for 6–9 passages before transfer to regeneration medium. The plants are then transferred to soil. No selection is performed at any step during this sequence.

In a second preferred sequence, callus is induced on a callus induction medium as described below. The callus induction medium could contain 0–0.2 mM AEC. If no AEC is contained in the callus induction medium, the callus is transferred to maintenance medium for 2–6 passages before it is transferred to selection medium. If the callus induction medium contains AEC, the callus is then transferred to selection medium rather than to maintenance medium. The callus is transferred to selection medium for 3–8 passages before transfer to regeneration medium. The concentration of AEC is increased stepwise from 0.1 to 3.0 mM, preferably from 0.1 to 1.0 mM or from 0.5 to 2.0 mM, through the passages. In an alternative, the AEC concentration is dropped to zero after a stepwise increase in concentration, i.e., transfer to a maintenance medium, and then raised to 1.5–2.5 mM, preferably 1.5–2.0 mM, in the next transfer before proceeding to regeneration medium. 2–4 passages, preferably 3 passages, on regeneration medium may be performed prior to transferring the plants to the soil. The regeneration medium may contain 0–0.5 mM AEC. It is preferred to utilize AEC in the regeneration medium and to lower its concentration stepwise through the passages on the regeneration medium.

The third preferred sequence is similar to the second sequence except that the concentration of AEC is increased stepwise from 1.0 to 3.0 mM, preferably from 1.0 to 2.0 mM, during the passages on the selection medium.

In a fourth preferred sequence, callus is induced on a callus induction medium as described above. The callus induction medium could contain 0–0.2 mM AEC. If no AEC is contained in the callus induction medium, the callus is transferred to maintenance medium for 2–6 passages before it is transferred to selection medium. If the callus induction medium contains AEC, the callus is then transferred to selection medium. The callus is transferred to selection medium for 3–8 passages before transfer to regeneration medium. The concentration of AEC may be 0.25–0.5 mM for 1–3 passages, preferably 2 passages, and then it is raised to 2.0–3.0 mM, preferably 2.0 mM, for 1–2 passages, preferably 1 passage. The AEC concentration is then lowered to 0.5 mM and increased stepwise to 1.0–1.5 mM over 3–6 passages, preferably 4 passages. In an alternative, the AEC concentration is dropped to zero after a stepwise increase in concentration, i.e., transfer to a maintenance medium and then raised to 1.5–2.0 mM in the next transfer before proceeding to regeneration medium. 2–4 passages, preferably 3 passages, on regeneration medium may be performed prior to transferring the plants to the soil. The regeneration medium may contain 0–0.5 mM AEC. It is preferred to utilize AEC in the regeneration medium and to lower its concentration stepwise through the passages on the regeneration medium.

The preferred sequences described above can be modified in accordance with the teachings herein and within the skill of the art. Several modifications include (a) reduced number of transfers on certain of the media, (b) addition of other media to the sequence, (c) use of other basal media well known in the art, (d) the deletion of the transfers to maintenance media, (e) addition of more transfers to maintenance media during the overall selection scheme, (f) reduced passage duration, (g) increased number of transfers on each medium, and (h) modification of AEC in sequence.

The plant tissue which is preferred for use in initiation of callus is the immature embryo. It is preferred to use an immature embryo from a plant which has an elevated level of lysine. Such maize lines include lines 1007, 1008, 1010 and 1012 of Crow's Hybrid Corn Company, Milford, Ill. The immature embryos are isolated from the cob at approximately 10–17 days post-pollination when the embryos are 1.0–2.0 mm, preferably 1.5 mm, in length. The cob is harvested and surface-sterilized. The immature embryos are isolated from each kernel. The embryos are plated onto callus induction medium which may or may not contain AEC. The embryos are plated so that the embryo axis is in contact with the medium, i.e., the scutellar side is up.

The callus induction medium comprises mineral salts, vitamins and sucrose. The mineral salts comprise macroelements and microelements. The macroelements used in the callus induction medium may be the following compounds: magnesium sulfate, calcium chloride, monopotassium phosphate, potassium nitrate and ammonium sulfate. The microelements contained in the callus induction medium are: boric acid, manganese sulfate, zinc sulfate, potassium iodide, iron (II) sulfate, disodium-ethylenediaminetetracetic acid (EDTA), sodium molybdate (VI), copper (II) sulfate and cobalt chloride. This combination of mineral salts is known in the art as the N6 mineral salts, which have been modified to contain mineral salts of copper, cobalt and molybdenum. Other combinations of mineral salts may also be used as long as they do not adversely affect callus induction. Examples of combinations of mineral salts include, but are not limited to, MS, Heller, Nitsch and Nitsch, B5 and White.

The preferred amounts of the macroelements and microelements used to prepare one liter of the callus induction medium are as follows: 185 mg magnesium sulfate heptahydrate, 166 mg calcium chloride dihydrate, 400 mg monopotassium phosphate, 2830 mg potassium nitrate, 463 mg ammonium sulfate, 1.6 mg boric acid, 4.4 mg manganese sulfate monohydrate, 1.5 mg zinc sulfate heptahydrate, 0.83 mg potassium iodide, 27.8 mg iron (II) sulfate heptahydrate, 37.3 mg disodium-EDTA, 0.25 mg sodium molybdate (VI) dihydrate, 0.025 mg copper (II) sulfate pentahydrate and 0.025 mg cobalt chloride hexahydrate.

The callus induction medium also contains vitamins. The vitamins used include myo-inositol, nicotinic acid, glycine, pyridoxine, thiamine, and pantothenate. The amounts of vitamins used to prepare one liter of the callus induction medium are as follows: 100 mg myo-inositol, 0.5 mg nicotinic acid, 2 mg glycine, 0.5 mg pyridoxine hydrochloride and 1.0 mg thiamine hydrochloride and 0.25 mg calcium pantothenate.

The first medium contains 2–6%, preferably 3%, sucrose and a gelling agent such as agar or Gelrite TM (trademark, Kelco Commercial Development, P.O. Box 23076, San Diego, Calif.). It is preferred to use Bacto-Agar at a concentration of about 0.78%. The medium has a pH of 5.5–6.0, with a preferred pH of 5.8, before autoclaving.

In addition to the above components, the callus induction medium also contains a hormone. As used herein, "hormone" is intended to mean any natural or synthetic compound which has a regulatory effect on plants or plant tissue. Plant hormones include auxins and cytokinins. The hormone which is useful for callus induction in the present invention is 2,4-D. 2,4-D can be utilized alone or in combination with another hormone such as 2,4,5-trichlorophenoxyacetic acid (2,4,5-T) or zeatin. Other hormones, such as those described in published European application No. 0 177 738 and copending U.S. application Ser. No. 865,431 filed May 21, 1986, now U.S. Pat. No. 4,665,030 issued May 12, 1987, can be used. The amount of hormone is sufficient to insure callus formation. Generally, about 2–3 mg/l of 2,4-D is sufficient, with 2 mg/l preferred. If zeatin or 2,4,5-T are also present, they can be utilized in an amount of 2–3 mg/l, preferably about 2 mg/l.

The callus induction medium may also contain a low concentration of AEC. It is preferred that no AEC be present in this medium. If AEC is present, it is preferred that a concentration of 0.05–0.2 mM be utilized.

The immature embryos are plated on the callus induction medium and cultured in diffused light with a photoperiod of 16 hours per day for 2–5 weeks, preferably 3–4 weeks. During this time, the embryo undergoes de-differentiation and callus formation. After culturing the immature embryo on the callus induction medium, the callus is transferred and subcultured on either a maintenance medium or a selection medium. Generally, the only difference between the maintenance medium and the selection medium is that the latter contains AEC. The callus may be cultured on the maintenance medium for 3–6 transfers before it is transferred to selection medium. The callus may be cultured on the selection medium for 3–8 transfers before it is transferred to regeneration medium. The callus is transferred to fresh maintenance or selection medium every 10–70 days.

The maintenance and selection media comprise mineral salts, vitamins, sucrose and a hormone in an amount sufficient to maintain the callus. The mineral salts and vitamins are as described for the callus induction medium. As in the callus induction medium, various combinations of mineral salts which do not adversely affect the functioning of the medium may be utilized. The sucrose concentration is 3–6%, preferably 3%. The hormone is generally 2,4-D at a concentration of 2–3 mg/l, preferably 2 mg/l, although others can be used as discussed above. Bacto-Agar at 0.78% is used to solidify the medium.

The maintenance and selection media may further contain L-glutamine and citric acid. If these components are utilized, it is preferred to use a concentration of 10 mM L-glutamine and 5 mM citric acid.

The selection medium further contains AEC. The concentration of AEC in the selection medium may range from 0.1–3.0 mM, preferably 0.1–2.0 mM. The concentration of AEC is varied during the selection process, as will be described further below.

After completing the selection sequence, the selected callus is placed on regeneration medium. One or more regeneration media may be utilized, with transfers to fresh regeneration medium occurring at about 5–40 days. Generally, 2–4 transfers may be utilized.

The regeneration medium comprises mineral salts, vitamins and sucrose. The mineral salts may be the same as for the callus induction medium, i.e., N6 salts, or they may be the MS mineral salts. It is preferred to utilize N6 salts.

The regeneration medium also contains vitamins. The vitamins which may be utilized are either (a) thiamine, nicotinic acid, pyridoxine and glycine, or (b) thiamine, glycine and myo-inositol. The (a) vitamins are referred to herein as N6 vitamins plus glycine, and the (b) vitamins are referred to herein as vitamin G. The amount of vitamins used to prepare one liter of regeneration medium is as follows: (a) for N6 vitamins: 1 mg thiamine hydrochloride, 0.5 mg nicotinic acid, 0.5 mg pyridoxine hydrochloride and 2 mg glycine; and (b) for vitamin G: 1 mg thiamine hydrochloride, 2 mg glycine and 100 mg myo-inositol.

It is preferred that the regeneration medium contains 2–6% sucrose, and the gelling substance may be Bacto-Agar or Gelrite at about 0.78% or about 0.22%, respectively.

The regeneration medium may contain AEC at a concentration of 0.1–0.50 mM. It is preferred to reduce the AEC concentration during the transfers which are performed at about 5–40 days during the regeneration cycle. The regeneration medium may also contain a hormone. It is preferred to utilize one or more cytokinins if a hormone is used. The hormone may be selected from a mixture of (a) 0.2–0.5 mg/l indoleacetic acid (IAA) and 0.4–1.5 mg/l benzyl amino purine (BAP), preferably either 0.3 mg/l and 1.0 mg/l, respectively, or 0.3 mg/l and 0.5 mg/l, respectively, or 0.25 mg/l and 1.0 mg/l, respectively; (b) 0.2–0.5 mg/l IAA and 0.8–1.5 mg/l BAP, preferably 0.3 mg/l and 1.0 mg/l, respectively; and (c) 0.1–0.3 mg/l 2,4-D, 0.05–0.2 mg/l BAP and 0.2–0.5 mg/l gibberellic acid (GA$_3$), preferably 0.2 mg/l, 0.1 mg/l and 0.35 mg/l, respectively.

After plants have been regenerated and established, they are transferred to cubes which contain one part of potting soil and one part of vermiculite. The gelling substance is washed off the plants prior to transfer to the cubes. The plants are transferred to 12" pots containing potting soil after about 4–40 days and placed in the greenhouse. All of the culturing described above and that described below in the examples is conducted at about 24° C. with a 16 hour diffused light/8 hour dark cycle.

In several instances, the $R_1$ seeds produced by plants obtained in accordance with the above process showed a decreased free pool lysine content. However, plants germinated from these $R_1$ seeds produced $R_2$ seeds having an average free pool lysine content of at least 325 μg per gram dry seed weight. Thus, a low free pool lysine content in $R_1$ seed does not indicate that the final desired characteristics cannot be obtained. It demonstrates that several generations of plants may be required to obtain plants and seeds having the desired characteristics.

The present invention will be further described by reference to the following non-limiting examples.

EXAMPLE 1

Preparation of Solutions

The following stock solutions or solutions were prepared for use in making the media described in further detail below.

1. OPA Reaction Mix

OPA reaction mix was prepared by dissolving 2.6 g of boric acid in 90 ml of deionized water. The pH was adjusted to 10.4 with a 45% solution of KOH. 200 μl of 2-mercaptoethanol was added, followed by 300 μl of Brij-35. Brij-35 was added to stabilize the OPA-lysine complex (*Anal.Biochem.* 101, 61 (1980)). 80 mg of Fluoropa (OPA from Pierce) was dissolved in 1 ml methanol and then added to the borate solution. The volume was adjusted to 100 ml with deionized water. The OPA reaction mix was kept at 4° C. and was discarded after two weeks to insure low background peaks.

2. AEC Stock Solution

A 500 mM stock solution of AEC was prepared by dissolving 5.02 g of AEC in 500 ml of deionized water or by dissolving 1.004 g of AEC in 100 ml of deionized water. The pH was adjusted to 5.8 using 1N KOH.

3. Hormones

A. 2,4-D. A 0.5 mg/ml stock solution was prepared by dissolving 50 mg of 2,4-D in 100 ml of deionized water.

B. IAA. A 0.5 mg/ml stock solution was prepared by dissolving 50 mg of IAA in 100 ml of deionized water.

C. BAP. A 0.5 mg/ml stock solution was prepared by dissolving 50 mg of BAP in 100 ml of deionized water.

D. Zeatin. A 0.1 mg/ml stock solution was prepared by dissolving 10 mg of zeatin in 100 ml of deionized water.

E. $GA_3$. A 0.167 mg/ml stock solution was prepared by dissolving 16.7 mg of $GA_3$ in 100 ml of deionized water.

F. 2,4,5-T. A 0.5 mg/ml stock solution was prepared by dissolving 50 mg of 2,4,5-T in 100 ml of deionized water.

4. Vitamins

A. N6 Vitamins. A 1000× stock solution of N6 vitamins was prepared by dissolving 100 mg of thiamine hydrochloride, 50 mg of nicotinic acid, 50 mg of pyridoxine hydrochloride and 200 mg of glycine in 100 ml of deionized water.

B. Vitamin G. A 1000× stock solution of vitamin G was prepared by dissolving 100 mg of thiamine hydrochloride, 200 mg of glycine and 10 g of myo-inositol in 100 ml of deionized water.

C. Vitamins. A 1000× stock solution of vitamins was prepared by dissolving 100 mg of thiamine hydrochloride, 50 mg of pyridoxine hydrochloride, 50 mg of nicotinic acid, 200 mg of glycine, 10 g of myo-inositol and 25 mg of calcium pantothenate in 100 ml of deionized water. The pH was adjusted to 5.8 using 1N KOH.

5. Amino Acids

A. Glutamine. A 250 mM stock solution was prepared by dissolving 3.65 g of L-glutamine in 100 ml of deionized water. The pH was adjusted to 5.8 with 1N KOH.

B. Citric Acid. A 1M stock solution was prepared by dissolving 19.2 g of anhydrous citric acid in 100 ml of deionized water. The pH was adjusted to 5.8 with 1N KOH.

6. Mineral Salts

A. Modified N6. A 20× stock solution of modified N6 salts was prepared by dissolving 1850 mg of magnesium sulfate heptahydrate, 1660 mg of calcium chloride dihydrate, 4.0 g of monopotassium phosphate, 4.63 g of ammonium sulfate, 28.3 g of potassium nitrate, 16 mg of boric acid, 44 mg of manganese sulfate monohydrate, 15 mg of zinc sulfate heptahydrate, 8 mg of potassium iodide, 278 mg of iron (II) sulfate heptahydrate, 373 mg of disodium-EDTA, 2.5 mg of sodium molybdate (VI) dihydrate, 0.25 mg of copper (II) sulfate pentahydrate and 0.25 mg of cobalt chloride hexahydrate in 300 ml of deionized water. The volume was then brought to 500 ml and divided into 50 ml aliquots.

B. MS. A 20× stock solution of MS salts was prepared by dissolving 10 packages of MS salts, unbuffered (Gibco Catalog No. 600-1117) in 500 ml of deionized water. The stock solution was divided into 50 ml aliquots.

EXAMPLE 2

Preparation of Media 1. 2D/Z3S. This medium was prepared by adding 30 g of sucrose, 50 ml of 20× modified N6 salts and 4 ml of 2,4-D stock solution to 600 ml of deionized water. The volume was brought up to 979 ml with deionized water. The pH was adjusted to 5.8 with 1N KOH, 7.8 g of Bacto-Agar were added, and the mixture was autoclaved. 20 ml of zeatin stock solution and 1 ml of vitamins stock solution were filter-sterilized and added to the cooling medium, which was poured into petri dishes.

2. 10T3S. This medium was prepared by adding 30 g of sucrose, 50 ml of 20× modified N6 salts, 4 ml of 2,4-D stock solution and 4.4 ml of 2,4,5-T stock solution to 600 ml of deionized water. The volume was brought up to 999 ml with deionized water and the pH adjusted to 5.8 with 1N KOH. 7.8 g of Bacto-Agar were added and the mixture autoclaved. 1 ml of vitamins stock solution was filter-sterilized and added to the cooling medium, which was poured into petri dishes.

3. 3NM. This medium was prepared by adding 30 g of sucrose, 50 ml of 20× modified N6 salts and 4 ml of 2,4-D stock solution to 600 ml of deionized water. Additional deionized water was added to bring the volume to 954 ml. The pH was adjusted to 5.8 using 1N KOH and 7.8 g of Bacto-Agar were added. The mixture was autoclaved for 20 minutes at 20 psi and 250° F. 40 ml of the glutamine stock solution, 5 ml of the citric acid stock solution, and 1 ml of the vitamins stock solution were each sterilized by filtration through a 0.22 micron Millipore membrane or a 0.2 micron Gelman filter and then added to the cooling medium, which was poured into petri dishes.

4. A0.2N. This medium was prepared as described for 3 NM except that the volume was brought up to 950 ml before autoclaving. 4 ml of the AEC stock solution was filter-sterilized and added to the cooling medium along with the glutamine, citric acid and vitamins.

5. A0.25N. This medium was prepared as described above except that the volume was brought up to 949 ml before autoclaving and 5 ml of AEC stock solution were used.

6. A0.5N. This medium was prepared as described above except that the volume was brought up to 944 ml before autoclaving and 10 ml of AEC stock solution were used.

7. A1N. This medium was prepared as described above except that the volume was brought up to 934 ml before autoclaving and 20 ml of AEC stock solution were used.

8. A2N. This medium was prepared as described above except that the volume was brought up to 914 ml before autoclaving and 40 ml of AEC stock solution were used.

9. A0.05N. This medium was prepared as described for A0.2N except that 1 ml of AEC stock solution was used and the initial volume brought up to 953 ml.

10. A0.1N. This medium was prepared as described for A0.2N except that 2 ml of AEC stock solution were used and the initial volume brought up to 952 ml.

11. 2N3. This medium was prepared by adding 30 g of sucrose, 50 ml of 20× modified N6 salts and 4 ml of 2,4-D stock solution to 600 ml of deionized water. Additional deionized water was added to bring the volume to 999 ml. The pH was adjusted to 5.8 using 1N KOH, and 7.8 g of Bacto-Agar were added. The mixture was autoclaved as previously described. 1 ml of the vitamins stock solution was filter-sterilized and added to the cooling medium, which was poured into petri dishes.

12. 2N6. This medium was prepared as described for 2N3 except that 60 g of sucrose were added instead of 30 g.

13. 3N3. This medium was prepared as described for 2N3 except that 6 ml of 2,4-D stock solution were added instead of 4 ml.

14. 3N. This medium was prepared by adding 30 g of sucrose, 50 ml of 20× modified N6 salts and 4 ml of 2,4-D stock solution to 600 ml of deionized water. Additional deionized water was added to bring the volume up to 954 ml. The pH was adjusted to 5.8 with 1N KOH and 7.7 g of Bacto-Agar were added. The mixture was autoclaved. 40 ml of glutamine stock solution, 5 ml of citric acid stock solution and 1 ml of vitamins stock solution were filter-sterilized and added to the cooling medium. The medium was poured into petri dishes.

15. MAC15. This medium was prepared as described for 2N3 except that the volume was brought up to 969 ml before autoclaving. 30 ml of AEC stock solution were filter-sterilized and added to the cooling medium along with the vitamins. The medium was then poured into petri dishes.

16. MAC20. This medium was prepared as described for MAC15 except that the volume was brought to 959 ml before autoclaving and 40 ml of AEC stock solution was used.

17. MAC10. This medium was prepared as described for MAC15 except that the volume before autoclaving was 979 ml and 20 ml of AEC stock solution were used instead of 30 ml.

18. RM1.5. This medium was prepared by adding 60 g of sucrose, 50 ml of 20× modified N6 salts and 1 ml of vitamin G stock solution to 600 ml of deionized water. The volume was brought up to 990 ml by the addition of deionized water. The pH was adjusted to 5.8 with 1N KOH, and 2.2 g of Gelrite were added. The mixture was autoclaved. 10 ml of AEC stock solution was filter-sterilized and added to the cooling medium. The mixture was then poured into petri dishes.

19. RM2.25. This medium was prepared by adding 20 g of sucrose, 50 ml of 20× modified N6 salts, 0.6 ml of IAA stock solution, 2.0 ml of BAP stock solution, and 1 ml of vitamin G stock solution to 600 ml of deionized water. The volume was brought up to 995 ml by the addition of deionized water. The pH was adjusted to 5.8 with 1N KOH, and 2.2 g of Gelrite were added. The mixture was autoclaved, and 5 ml of AEC stock solution was filter-sterilized and added to the cooling medium. The mixture was then poured into petri dishes.

20. RM(2). This medium was prepared as described for RM2.25 except that the volume was brought to 1 l and AEC was not added.

21. RM1.25. This medium was prepared as described for RM1.5 except that the volume was brought to 995 ml before autoclaving and 5 ml of AEC stock solution were used instead of 10 ml.

22. HV12A. This medium was prepared by adding 20 g of sucrose, 1 package of Gibco MS salts (Catalog No. 500-117), 0.4 ml of 2,4-D stock solution and 0.2 ml of BAP stock solution to 600 ml of deionized water. The volume was brought up to 992.9 ml with the addition of deionized water. The pH was adjusted to 5.8 with 1N KOH and 2 g of Gelrite were added. The mixture was autoclaved. 5 ml of AEC stock solution and 2.1 ml of $GA_3$ stock solution were each filter-sterilized and added to the cooling medium. The mixture was then poured into petri dishes.

23. RRM. This medium was prepared by adding 15 g of sucrose, 50 ml of 20× MS salts, 1 ml of vitamin stock solution and 0.2 ml of 2,4-D stock solution to 600 ml of deionized water. The volume was brought up to 1 l by the addition of deionized water, and the pH adjusted to 5.8 with 1N KOH. 8.5 g of Bacto-Agar were added. The mixture was autoclaved and poured into plant and tissue culture containers (Flow general Company Catalog No. 26-721-07).

24. RRM1. This medium was prepared as described for RRM except that the volume was brought up to 998 ml. 2 ml of AEC stock solution were filter-sterilized and added to the cooling medium before it was poured.

25. IBM. This medium was prepared by adding 30 g of sucrose, 50 ml of 20× MS salts, 1 ml of vitamin G stock solution, 0.6 ml of IAA stock solution and 2 ml of BAP stock solution to 600 ml of deionized water. Deionized water was added to bring the volume to 1 l. The pH was adjusted to 5.8 with 1N KOH, and 8.3 g of Bacto-Agar were added. The mixture was heated to dissolve the agar, and poured into test tubes so that the test tubes were one-third full. The tubes were then autoclaved as described above.

26. IBM7. This medium was prepared as described for IBM except that 1 ml of BAP stock solution were used instead of 2 ml of BAP stock solution.

27. IBM12. This medium was prepared as described for IBM except that 0.5 ml of IAA stock solution was used instead of 0.6 ml.

EXAMPLE 3

Immature Embryo Isolation

Immature embryos were isolated from the cob of corn from lines 1007, 1008, 1010 or 1012 of Crow's Hybrid Corn Company, Milford, Ill., 10-17 days post-pollination, when they were 1-2 mm, preferably 1.5 mm, in length. The cob was harvested and surface-sterilized in a 20% solution of bleach and 1 drop of Liquinox ® (Alconox Inc., 853 Broadway, New York, N.Y.) detergent for 20 minutes. The cobs were rinsed with sterile, deionized water. The immature embryos were isolated by slicing off the top of each kernel with a scalpel and scooping out the endosperm. The immature embryos were then taken out and plated onto the desired medium, as described below, so that the embryo axis was in contact with the medium, i.e., the scutellar side was up.

EXAMPLE 4

Basic Culturing Conditions and Corn Growth

Immature embryos isolated as described above were plated onto a medium in a petri dish for the initiation of callus so that the embryo axis was in contact with the medium, i.e., the scutellar side was up. Various media were utilized for callus initiation, including 2D/Z3S, 10T3S, A0.05N, A0.2N, 3N and 2N6. All culturing was conducted with a 16 hour diffused light/8 hour dark cycle at about 24° C. The immature embryo was cultured for about 21 to about 32 days before transferring to fresh medium. Transfers to fresh medium were usually performed after about 6 to about 67 days. Various sequences of media were utilized as described in detail below. Generally, the callus was selected for a period of time on medium containing AEC, and then plants were regenerated. Regeneration was performed using several regenerating media, including RM1.5, RM2.25, RM1.25, RM(2), RRM, IBM12, IBM7, RRM1 and HV12A. A sequence of one or more of these media were utilized as described in further detail below. After plants were obtained, they were transferred to soil contained in cubes. The soil was comprised of a 1:1 mixture of vermiculite and potting soil. After about 4 to about 30 days, each plant was transferred to a 12" pot containing standard nursery potting soil and placed in the greenhouse.

The plants were grown in the greenhouse and self-pollinated. The $R_1$ seeds were collected and assayed for free pool lysine content. $R_1$ seeds were also planted in a field research nursery. The $R_1$ plants were self-pollinated and $R_2$ seeds collected.

EXAMPLE 5

Culture Sequences

Immature embryos isolated as previously described were cultured and plants regenerated as follows. All culturing was conducted with a 16 hour diffused light/8 hour dark cycle.

1. Line 1012 (Tissue Culture Control)

Immature embryos were plated on 3N medium. The callus was transferred and plants regenerated by the following sequence: to 3N medium after 26 days, to 3N medium after 67 days, to 3NM medium after 21 days, to 3NM medium after 32 days, to 3NM medium after 28 days, to 3NM medium after 29 days, to 3NM medium after 28 days, to RM(2) medium after 29 days, to cubes after 18 days, and to 12" pots after 29 days. One plant was identified as CZ9C22C*. The $R_1$ seeds from this plant were assayed for free pool lysine.

2. Line 1007

Immature embryos were plated on A0.2N medium. The callus was transferred and plants regenerated by the following sequence: to A0.25N medium after 21 days, to A0.5N medium after 25 days, to A1N medium after 30 days, to A1N medium after 25 days, to HV12A medium after 22 days, to IBM7 medium after 7 days, to RRM medium after 23 days, to cubes after 53 days, and to 12" pots after 13 days. One plant was identified as CZ14I8A6, and the $R_1$ seeds were assayed for free pool lysine.

3. Line 1012

Immature embryos were plated on 3N medium. The callus was transferred and plants regenerated by the following sequence: to 3N medium after 31 days, to 3N medium after 32 days, to 3N medium after 35 days, to A0.25N medium after 19 days, to A0.25N medium after 33 days, to A0.5N medium after 28 days, to A0.5N medium after 29 days, to A1N medium after 29 days, to A1N medium after 31 days, to A1N medium after 11 days, to RM1.25 medium after 19 days, to RM2.25 medium after 9 days, to RRM medium after 29 days, to cubes after 12 days, and to 12" pots after 7 days. One plant was identified as CZ9D15C1-3.

4. Line 1012

Immature embryos were plated on 3N medium. The callus was transferred and plants regenerated by the following sequence: to 3N medium after 28 days, to 3N medium after 28 days, to 3N3 medium after 30 days, to 3N medium after 37 days, to A0.25N medium after 19 days, to A0.25N medium after 33 days, to A0.5N medium after 28 days, to A0.5N medium after 29 days, to A1N medium after 24 days, to A1N medium after 26 days, to A1N medium after 21 days, to RM1.25 medium after 19 days, to RM2.25 medium after 9 days, to IBM12 medium after 6 days, to RRM medium after 13 days, to cubes after 23 days, and to 12" pots after 13 days. One plant was identified as CZ9A3B1B9. A second plant identified as CZ9A3B1B11 was produced by the same sequence. $R_1$ seeds from these two plants were assayed for free pool lysine. A third plant was identified as CZ9A3B1A6. The $R_1$ seeds from the third plant were grown and the $R_2$ seeds were analyzed for free pool lysine.

5. Line 1012

Immature embryos were plated on 3N medium. The callus was transferred and plants regenerated by the following sequence: to 3N medium after 26 days, to 3N medium after 30 days, to 3N medium after 37 days, to A0.25N medium after 19 days, to A0.25N medium after 33 days, to A2N medium after 21 days, to A0.5N medium after 33 days, to A0.5N medium after 16 days, to A1N medium after 25 days, to A1N medium after 33 days, to RM1.25 medium after 19 days, to RM2.25 medium after 9 days, to RRM medium after 16 days, to cubes after 12 days, and to 12" pots after 22 days. Seven different plants were identified as: CZ9B9A1A1, CZ9B9A1A6, CZ9B9A1B5, CZ9B9A1B+, CZ9A-3A4-3, CZ9A3A4-6, and CZ9C27C2A4. The $R_1$ seeds from these plants were analyzed for free pool lysine. An additional plant identified as CZ9C27C2A17 was used to produce $R_2$ seeds which were assayed for free pool lysine.

6. Line 1010

Immature embryos were plated on 2N6 medium. The callus was transferred and plants regenerated by the following sequence: to 2N6 medium after 32 days, to 2N3 medium after 27 days, to 3NM medium after 11 days, to 3NM medium after 27 days, to A0.5N medium after 33 days, to A0.5N medium after 41 days, to A1N medium after 28 days, to A1N medium after 26 days, to MAC20 medium after 51 days, to MAC15 medium after 32 days, to RM1.5 medium after 44 days, to RM2.25 medium after 7 days, to RRM1 medium after 33 days, to cubes after 32 days, and to 12" pots after 4 days. Two individual plants were identified as CZ11C8A2D and CZ11C8A2E. $R_1$ seeds from these plants were assayed for free pool lysine.

7. Line 1010

Immature embryos were plated on 2D/Z3S medium. The callus was transferred and plants regenerated by the following sequence: to 2N6 medium after 32 days, to 2N3 medium after 27 days, to 3NM medium after 11 days, to 3NM medium after 27 days, to A0.5N medium after 33 days, to A0.5N medium after 41 days, to A1N medium after 29 days, to A1N medium after 23 days, to A1N medium after 26 days, to MAC20 medium after 51 days, to 2N3 medium after 30 days, to MAC15 medium after 32 days, to RM1.25 medium after 44 days, to RM2.25 medium after 7 days, to cubes after 33 days, and to 12" pots after 22 days. Four different plants were identified as CZ11C19A1A1B, CZ11C19B2A7, CZ11C19B2A8 and CZ11C19B2A10. The $R_1$ seeds were analyzed for free pool lysine.

8. Line 1010

Immature embryos were plated on either 10T3S medium (CZ11C18) or 2D/Z3S medium (CZ11C19). The callus was transferred and plants regenerated by the following sequence: to 2N6 medium after 32 days, to 2N3 medium after 27 days, to 3NM medium after 11 days, to 3NM medium after 27 days, to A0.5N medium after 33 days, to A0.5N medium after 41 days, to A1N medium after 29 days, to A0.5N medium after 23 days, to A0.5N medium after 26 days, to MAC10 medium after 51 days, to 2N3 medium after 30 days, to MAC15 medium after 32 days, to RM1.5 medium after 44 days, to RM2.25 medium after 7 days, to RRM1 medium after 33 days, to cubes after 22 days, and to 12" pots after 4 days. Five plants were identified as CZ11C18B1C1, CZ11C18B2C1, CZ11C19A1B1B, CZ11C19A1B1C and CZ11C19A1B2B. $R_1$ seeds were assayed for free pool lysine.

9. Line 1010

Immature embryos were plated on 2N6 medium. The callus was transferred and plants regenerated by the following sequence: to 2N6 medium after 32 days, to 2N3 medium after 27 days, to 3NM medium after 11 days, to 3NM medium after 27 days, to 3NM medium after 33 days, to A1N medium after 48 days, to A1N medium after 32 days, to A1N medium after 13 days, to A1N medium after 35 days, to MAC20 medium after 52 days, to 2N3 medium after 30 days, to MAC15 medium after 32 days, to RM1.25 medium after 44 days, to RM2.25 medium after 7 days, to RRM1 medium after 33 days, to cubes after 22 days, and to 12" pots after 14 days. One plant was identified as CZ11C9C2, and $R_1$ seeds were assayed for free pool lysine.

10. Line 1008

Immature embryos were plated on A0.5N medium. The callus was transferred and plants regenerated by the following sequence: to A0.1N medium after 36 days, to A0.25N medium after 33 days, to A0.5N medium after 22 days, to A1N medium after 32 days, to A1N medium after 23 days, to A1N medium after 28 days, to RM1.25 medium after 20 days, to RM2.25 medium after 8 days, to IBM7 medium after 6 days, to RRM medium after 13 days, to cubes after 24 days, and to 12" pots after 11 days. One plant was identified as CZ13FC1-16, which was used to produce $R_2$ seeds. The $R_2$ seeds were assayed for free pool lysine.

Following similar procedures as described above, the following plants were also obtained: CZ9D15D2; CZ9C27A1-8; CZ9C27C2A7; CZ9C27C2A9; CZ9C27C2A18A; CZ9C22A1B1H; CZ9A20C11; CZ9BB48B; CZ9HH2A; CZ11C18B2C6; CZ11C8A2G; CZ11C20A1; CZ11K8B2C; CZ11C19A1B1, and CZ11.

EXAMPLE 6

Free Lysine Analysis of Corn Seed

A non-destructive single seed assay was used to determine the endogenous free lysine (endogenous free pool lysine) content of corn seed of the present invention. In this assay, corn kernels were soaked for 24 hours in sterile water. After soaking, some of the endosperm was removed with a scalpel, being careful not to nick the embryo. The embryo was placed into a clean tube so that it could be later planted. The pericarp was removed from around the excised endosperm and discarded. The endosperm fragments were placed into a mortar and pulverized thoroughly with a pestle. The pulverized endosperm was baked to dryness at 100° C. for one hour. 40 mg of the dried powder was added to a microfigure tube. A 5% solution of trichloroacetic acid (TCA) was added to each sample to obtain a final concentration of 10 $\mu$l TCA/mg tissue. The mixture was mixed thoroughly and allowed to sit for at least 30 minutes at room temperature, preferably with continuous shaking. The samples were spun for 10 minutes in a cold room microfuge. 30 $\mu$l of the supernatant were removed and added to a small glass tube or a new microfuge tube. 90 $\mu$l of OPA reaction mix were then added and the tube vortex mixed.

The mixture was then immediately subjected to reverse-phase high pressure liquid chromatography to separate the OPA-amino acid derivatives. A Perkin-Elmer C18 column, 3$\mu$ particle size, was utilized. 50 $\mu$l of the sample were injected into the sample loop to insure filling the loop. The OPA-amino acid derivatives were eluted with a solvent consisting of 30% acetonitrile and 70% 50 mM potassium phosphate, pH 6.5, with a flow rate of 1.5 ml/min. The OPA-amino acid derivatives were detected by absorbance at 340 nm. Data collection was started at 0.1 minute and completed at 9 minutes. The detection threshold was 1.00 and the minimum peak width was 9.5. The area reject threshold was 2,000 and the vertical scale was 200 m volts. Appropriate control assays were performed to insure complete lysine extraction, OPA derivatization and detection sensitivity.

The free pool lysine content of individual seeds and the average free pool lysine content of seeds from individual plants are shown in Tables 1 and 2, respectively.

TABLE 1

Free Pool Lysine Content of Individual Seeds From Plants Produced in Example 5

| Plant Designation | Lysine (μg/gm Dry Seed Weight) | |
|---|---|---|
| | $R_1$ Seed | $R_2$ Seed |
| CZ14I8A6 | 555.61 | — |
| | 676.00 | — |
| | 531.00 | — |
| CZ9C22C* | 508.00 | — |
| CZ9D15C1-3 | 514.95 | — |
| | 501.00 | — |
| | 800.00 | — |
| CZ9A3B1B9 | 510.00 | — |
| CZ9A3B1B11 | 565.00 | — |
| CZ9B9A1A6 | 504.08 | — |
| | 718.00 | — |
| CZ9B9A1B5 | 719.39 | — |
| CZ9B9A1B30 | 673.23 | — |
| | 702.00 | — |
| | 735.00 | — |
| | 737.00 | — |
| CZ9A3A4-3 | 534.18 | — |
| | 551.00 | — |
| CZ9A3A4-6 | 888.77 | — |
| | 529.00 | — |
| | 510.00 | — |
| | 653.00 | — |
| CZ9C27C2A4 | 655.00 | — |
| CZ11C8A2D | 524.08 | — |
| | 504.06 | — |
| CZ11C8A2E | 549.13 | — |
| CZ11C19A1A1B | 503.76 | — |
| | 523.04 | — |
| | 500.07 | — |
| CZ11C19A1B2B | 525.07 | — |
| | 681.55 | — |
| | 532.00 | — |
| CZ11C19B2A7 | 580.74 | — |
| | 550.09 | — |
| | 693.88 | — |
| | 566.32 | — |
| CZ11C19B2A8 | 524.87 | — |
| | 656.06 | — |
| CZ11C19B2A10 | 652.68 | — |
| | 527.08 | — |
| | 664.08 | — |
| | 537.65 | — |
| CZ11C18B1C1 | 549.30 | — |
| | 644.73 | — |
| | 889.64 | — |
| CZ11C18B2C1 | 566.12 | — |
| CZ11C19A1B1A | 504.84 | — |
| CZ11C19A1B1B | 520.13 | — |
| | 574.81 | — |
| CZ11C19A1B1C | 505.35 | — |
| CZ11C9C2 | 502.51 | — |
| CZ13F1C1-16 | — | 593.05 |
| | — | 634.56 |
| CZ9A3B1A6 | — | 529.72 |
| CZ9C27C2A17 | — | 499.41 |
| | — | 521.65 |

TABLE 2

Average Free Pool Lysine Content of Seeds From Plants Produced in Example 5

| Plant Designation | Average Lysine (μg/gm Dry Seed Weight) | |
|---|---|---|
| | $R_1$ Seeds | $R_2$ Seeds |
| CZ14I8A6 | 464.09 | — |
| CZ9C22C* | 410.44 | — |
| CZ9C22A1B1H | 331.31 | — |
| CZ9A20C11 | 346.52 | — |
| CZ9D15C1-3 | 562.49 | — |
| CZ9B9A1A1 | 441.04 | — |
| CZ9B9A1A6 | 544.69 | — |
| CZ9B9A1B5 | 425.35 | — |
| CZ9BA1B30 | 711.81 | — |
| CZ9A3A4-3 | 473.55 | — |
| CZ9A3A4-6 | 645.19 | — |
| CZ9C27C2A4 | 330.12 | — |
| CZ9BB48A | 329.49 | — |
| CZ9HH2A | 333.28 | — |
| CZ11CBA2D | 443.25 | — |
| CZ11C8A2E | 420.13 | — |
| CZ11C8A2G | 401.57 | — |
| CZ11C19A1A1B | 483.21 | — |
| CZ11C19A1B2B | 541.89 | — |
| CZ11C19B2A7 | 597.76 | — |
| CZ11C19B2A8 | 466.14 | — |
| CZ11C19B2A10 | 595.37 | — |
| CZ11C20A1 | 359.49 | — |
| CZ11K8B2C | 364.87 | — |
| CZ11C18B1C1 | 625.78 | — |
| CZ11C18B2C1 | 462.99 | — |
| CZ11C19A1B1B | 462.13 | — |
| CZ11C19A1B1C | 377.10 | — |
| CZ11C19A1B1D | 418.19 | — |
| CZ11C9C2 | 427.50 | — |
| CZ11 | 444.70 | — |
| CZ13F1C1-16 | — | 540.28 |
| CZ9D15D2 | — | 342.70 |
| CZ9C27A1-8 | — | 427.10 |
| CZ9A3B1B9 | — | 327.14 |
| CZ9A3B1A6 | — | 391.46 |
| CZ9C27C2A9 | — | 376.47 |
| CZ9C27C2A17 | — | 450.35 |
| CZ9C27C2A18A | — | 358.12 |
| CZ9C27C2A7 | — | 361.25 |

The lysine content of the starting lines is shown in Table 3 below.

TABLE 3

Lysine Content of Starting Lines

| Line | Lysine Content (μg/gm Dry Seed Weight) | |
|---|---|---|
| | Individual Seeds | Average |
| 1007 | 5.00 | 25.12 |
| | 12.50 | |
| | 16.30 | |
| | 22.59 | |
| | 69.21 | |
| 1008 | 198.00 | 257.28 |
| | 267.00 | |
| | 278.00 | |
| | 182.28 | |
| | 361.13 | |
| 1010 | 331.96 | 281.18 |
| | 188.72 | |
| | 220.30 | |
| | 304.77 | |
| | 284.62 | |
| | 372.13 | |
| | 356.51 | |
| | 303.95 | |
| | 434.89 | |
| | 188.90 | |
| | 272.85 | |
| | 147.04 | |
| | 320.39 | |
| | 271.05 | |
| | 200.90 | |

TABLE 3-continued

Lysine Content of Starting Lines

| Line | Lysine Content (μg/gm Dry Seed Weight) Individual Seeds | Average |
|---|---|---|
| | 257.15 | |
| | 235.79 | |
| | 310.08 | |
| | 308.33 | |
| | 313.22 | |
| 1012 | 146.60 | 142.26 |
| | 100.40 | |
| | 165.82 | |
| | 74.74 | |
| | 223.75 | |

The preceding tables demonstrate the production of maize seeds which individually have a free pool lysine content of at least 500 μg per gram dry tissue weight and of maize plants which produce seeds having an average free pool lysine content of at least 325 μg per gram dry tissue weight.

Seeds of the lines Crow's 992 (CZ9D15C1-3) and Crow's 1085 (CZ9A3A4-6) were deposited on Aug. 5, 1986 with In Vitro International, Inc., Linthicum, Maryland 21090, and assigned the designated numbers IVI-10114 and IVI-10115, respectively.

While the invention has been described in connection with specific embodiments thereof, it will be understood that it is capable of further modifications. This application is intended to cover any variations, uses or adaptation of the invention following in general, the principles of the invention and including such departures from the present disclosure as come within known and customary practice within the art to which the invention pertains.

What is claimed is:

1. A process for increasing free pool lysine content of maize seed to at least 500 μg per gram dry seed weight, or increasing an average free pool lysine content of seeds produced by a maize plant to at least 325 μg per gram dry seed weight, said process comprising:
   (a) culturing immature embryo obtained from a maize plant on a callus induction medium comprising mineral salts, vitamins, sucrose and an auxin as a hormone to form callus;
   (b) subculturing the callus on a selection medium comprising mineral salts, vitamins, sucrose, S-2-aminoethyl-L-cysteine and an auxin as a hormone to produce callus resistant to S-2-aminoethyl-L-cysteine; and
   (c) subculturing the resistant callus on regeneration medium comprising mineral salts, vitamins and sucrose to regenerate plants.

2. The process of claim 1 which further comprises the step of:
   (a') subculturing the callus on a maintenance medium comprising mineral salts, vitamins, sucrose and an auxin as a hormone to maintain the callus before subculturing on the selection medium.

3. The process of claim 1 which includes 3–8 subculturing steps on selection medium.

4. The process of claim 2 which includes 2–6 subculturing steps on maintenance medium.

5. The process of claim 4 which includes 3–8 subculturing steps on selection medium.

6. The process of claim 5 wherein the S-2-aminoethyl-L-cysteine concentration in the selection medium is increased stepwise from about 0.1 mM to about 3.0 mM during the subculturing steps.

7. The process of claim 6 wherein the concentration is increased from about 0.5 mM to about 3.0 mM.

8. The process of claim 6 wherein the concentration is increased from about 1.0 mM to about 3.0 mM.

9. The process of claim 5 wherein the S-2-aminoethyl-L-cysteine concentration in the selection medium is increased stepwise from about 0.1 mM to about 3.0 mM during the subculturing steps.

10. The process of claim 9 wherein the concentration is increased from about 0.5 mM to about 3.0 mM.

11. The process of claim 9 wherein the concentration is increased from about 1.0 mM to about 3.0 mM.

12. The process of claim 3 wherein the S-2-aminoethyl-L-cysteine concentration in the selection medium is about 0.25–0.50 mM for 1–3 subculturing steps, about 2.0–3.0 mM for 1–2 subculturing steps, and raised stepwise from about 0.5 mM to about 1.0–1.5 mM for the final subculturing steps.

13. The process of claim 5 wherein the S-2-aminoethyl-L-cysteine concentration in the selection medium is about 0.25–0.50 mM for 1–3 subculturing steps, about 2.0–3.0 mM for 1–2 subculturing steps, and raised stepwise from about 0.5 mM to about 1.0–1.5 mM for the final subculturing steps.

14. The process of claim 6 wherein the S-2-aminoethyl-L-cysteine concentration is dropped to 0 mM for 1 subculturing step after the stepwise increase and then raised to about 1.5–2.5 mM for 1 subculturing step.

15. The process of claim 9 wherein the S-2-aminoethyl-L-cysteine concentration is dropped to 0 mM for 1 subculturing step after the stepwise increase and then raised to about 1.5–2.5 mM for 1 subculturing step.

16. The process of claim 1 which includes 2–4 subculturing steps on regeneration medium.

17. The process of claim 2 which includes 2–4 subculturing steps on regeneration medium.

18. The process of claim 16 which includes 3–8 subculturing steps on selection medium.

19. The process of claim 16 which includes 2–6 subculturing steps on maintenance medium.

20. The process of claim 19 which includes 3–8 subculturing steps on selection medium.

21. The process of claim 18 wherein the S-2-aminoethyl-L-cysteine concentration in the selection medium is increased stepwise from about 0.1 mM to about 3.0 mM during the subculturing steps.

22. The process of claim 21 wherein the concentration is increased from about 0.5 mM to about 3.0 mM.

23. The process of claim 21 wherein the concentration is increased from about 1.0 mM to about 3.0 mM.

24. The process of claim 20 wherein the S-2-aminoethyl-L-cysteine concentration in the selection medium is increased stepwise from about 0.1 mM to about 3.0 mM during the subculturing steps.

25. The process of claim 24 wherein the concentration is increased from about 0.5 mM to about 3.0 mM.

26. The process of claim 25 wherein the concentration is increased from about 1.0 mM to about 3.0 mM.

27. The process of claim 18 wherein the S-2-aminoethyl-L-cysteine concentration in the selection medium is about 0.25–0.50 mM for 1–3 subculturing steps, about 2.0–3.0 mM for 1–2 subculturing steps, and raised stepwise from about 0.5 mM to about 1.0–1.5 mM for the final subculturing steps.

28. The process of claim 20 wherein the S-2-aminoethyl-L-cysteine concentration in the selection medium is about 0.25–0.50 mM for 1–3 subculturing steps, about 2.0–3.0 mM for 1–2 subculturing steps, and raised stepwise from about 0.5 mM to about 1.0–1.5 mM for the final subculturing steps.

29. The process of claim 21 wherein the S-2-aminoethyl-L-cysteine concentration is dropped to 0 mM for 1 subculturing step after the stepwise increase and then raised to about 1.5–2.5 mM for 1 subculturing step.

30. The process of claim 24 wherein the S-2-aminoethyl-L-cysteine concentration is dropped to 0 mM for 1 subculturing step after the stepwise increase and then raised to about 1.5–2.5 mM for 1 subculturing step.

31. The process of claim 21 wherein the regeneration medium further comprises S-2-aminoethyl-L-cysteine.

32. The process of claim 24 wherein the regeneration medium further comprises S-2-aminoethyl-L-cysteine.

33. The process of claim 27 wherein the regeneration medium further comprises S-2-aminoethyl-L-cysteine.

34. The process of claim 28 wherein the regeneration medium further comprises S-2-aminoethyl-L-cysteine.

35. The process of claim 29 wherein the regeneration medium further comprises S-2-aminoethyl-L-cysteine.

36. The process of claim 30 wherein the regeneration medium further comprises S-2-aminoethyl-L-cysteine.

37. The process of claim 31 wherein the S-2-aminoethyl-L-cysteine concentration is decreased stepwise from 0.5 mM to 0.1 mM.

38. The process of claim 32 wherein the S-2-aminoethyl-L-cysteine concentration is decreased stepwise from 0.5 mM to 0.1 mM.

39. The process of claim 33 wherein the S-2-aminoethyl-L-cysteine concentration is decreased stepwise from 0.5 mM to 0.1 mM.

40. The process of claim 36 wherein the S-2-aminoethyl-L-cysteine concentration is decreased stepwise from 0.5 mM to 0.1 mM.

41. The process of claim 35 wherein the S-2-aminoethyl-L-cysteine concentration is decreased stepwise from 0.5 mM to 0.1 mM.

42. The process of claim 36 wherein the S-2-aminoethyl-L-cysteine concentration is decreased stepwise from 0.5 mM to 0.1 mM.

43. The process of claim 21 wherein the regeneration medium further comprises one or more cytokinins.

44. The process of claim 24 wherein the regeneration medium further comprises one or more cytokinins.

45. The process of claim 27 wherein the regeneration medium further comprises one or more cytokinins.

46. The process of claim 28 wherein the regeneration medium further comprises one or more cytokinins.

47. The process of claim 29 wherein the regeneration medium further comprises one or more cytokinins.

48. The process of claim 30 wherein the regeneration medium further comprises one or more cytokinins.

49. The process of claim 31 wherein the regeneration medium further comprises one or more cytokinins.

50. The process of claim 32 wherein the regeneration medium further comprises one or more cytokinins.

51. The process of claim 33 wherein the regeneration medium further comprises one or more cytokinins.

52. The process of claim 34 wherein the regeneration medium further comprises one or more cytokinins.

53. The process of claim 35 wherein the regeneration medium further comprises one or more cytokinins.

54. The process of claim 36 wherein the regeneration medium further comprises one or more cytokinins.

* * * * *